US006698162B2

United States Patent
Shudo et al.

(10) Patent No.: US 6,698,162 B2
(45) Date of Patent: Mar. 2, 2004

(54) METHODS OF PRODUCING A TERMINALLY STERILIZED TOPICAL PATCH PREPARATION

(75) Inventors: Jutaro Shudo, San Jose, CA (US); Larry Caldwell, San Jose, CA (US); Tu Xuan Duong, Milpitas, CA (US)

(73) Assignee: Teikoku Pharma USA, Inc., Campbell, CA (US)

( * ) Notice: Subject to any disclaimer, the term of this patent is extended or adjusted under 35 U.S.C. 154(b) by 86 days.

(21) Appl. No.: 09/813,652

(22) Filed: Mar. 20, 2001

(65) Prior Publication Data

US 2002/0005028 A1 Jan. 17, 2002

Related U.S. Application Data

(60) Provisional application No. 60/191,608, filed on Mar. 23, 2000, and provisional application No. 60/218,220, filed on Jul. 14, 2000.

(51) Int. Cl.$^7$ ................................................ B65B 63/00
(52) U.S. Cl. .............................. 53/428; 422/21; 422/22
(58) Field of Search .............................. 53/428; 422/21, 422/22, 23, 24, 40; 424/448

(56) References Cited

U.S. PATENT DOCUMENTS

| | | | | |
|---|---|---|---|---|
| 3,797,494 A | * | 3/1974 | Zaffaroni | |
| 3,940,325 A | * | 2/1976 | Hirao | |
| 4,250,139 A | * | 2/1981 | Luck et al. | 422/21 |
| 4,460,445 A | * | 7/1984 | Rekers | |
| 4,515,666 A | * | 5/1985 | Rekers | |
| 4,540,416 A | * | 9/1985 | Hattori et al. | |
| 4,652,763 A | | 3/1987 | Nablo | |
| 4,726,928 A | * | 2/1988 | Ejk et al. | 422/22 |
| 5,011,660 A | | 4/1991 | Arena | |
| 5,082,663 A | | 1/1992 | Konishi et al. | |
| 5,116,621 A | | 5/1992 | Oji et al. | |
| 5,242,951 A | | 9/1993 | Akemi et al. | |
| 5,480,649 A | | 1/1996 | Akazawa et al. | |
| 5,496,302 A | | 3/1996 | Minshall et al. | |
| 5,730,933 A | | 3/1998 | Peterson | |
| 5,782,914 A | | 7/1998 | Schankereli | |
| 5,827,529 A | | 10/1998 | Ono et al. | |
| 6,028,242 A | | 2/2000 | Tucker et al. | |
| 6,030,554 A | | 2/2000 | Ichihara | |

* cited by examiner

*Primary Examiner*—Mickey Yu
*Assistant Examiner*—Sameh Tawfik
(74) *Attorney, Agent, or Firm*—Bret E. Field; Bozicevic, Field & Francis LLP

(57) ABSTRACT

Methods of producing a terminally sterilized topical patch preparation are provided. In the subject methods, a topical patch preparation is exposed to electron beam radiation, preferably low level electron beam radiation, for a period of time sufficient to terminally sterilize the topical patch preparation. Also provided are the terminally sterilized topical patch preparations produced by the subject methods and methods of using the same.

5 Claims, No Drawings

METHODS OF PRODUCING A TERMINALLY STERILIZED TOPICAL PATCH PREPARATION

CROSS REFERENCE TO RELATED APPLICATIONS

Pursuant to 35 U.S.C. §119 (e), this application claims priority to the filing date of the U.S. Provisional Patent Application Ser. No. 60/191,608 filed Mar. 23, 2000 and Ser. No. 60/218,220, filed on Jul. 14, 2000; the disclosures of which are herein incorporated by reference.

INTRODUCTION

1. Field of the Invention

The field of this invention is transdermal drug delivery, particularly, methods of producing topical patch preparations for transdermal drug delivery.

2. Background of the Invention

Transdermal delivery devices, e.g., topical patches, wound dressings, etc., are used to administer a variety of therapeutic agents, such as pharmaceutically active agents. The devices are generally applied to the surface of the skin and a therapeutically active agent contained therein is delivered to the systemic circulation via absorption through the skin. Advantages of transdermal delivery of a therapeutic agent over oral or parenteral administration include increased bioavailability (as first-pass liver metabolism is avoided), and more controlled (e.g., sustained, continuous) delivery. Topical preparations, e.g., topical patch preparations, for transdermal delivery typically contain an active agent dissolved or dispersed in an aqueous adhesive gel composition that is coated or spread onto a fibrous material.

Sterile topical patch preparations for transdermal delivery are currently commercially produced by clean room fabrication from sterilized components. The process requires specially designed facilities, special equipment, protective clothing for clean room personnel made of special materials (e.g., Tyvek®); and stringent environmental control and maintenance, e.g., of air quality, pressure, temperature and humidity. Accordingly, clean room fabrication is costly.

Accordingly, the development of methods of producing terminally sterilized topical patch preparations for transdermal delivery would be of great benefit in drug delivery.

3. Relevant Literature

Patents of interest include the following: 6,030,554; 6,028,242; 5,782,914; 5,730,933; 5,496,302; 5,011,660 and 4,652,763. See also U.S. Pat. Nos. 5,827,529; 5,480,649; 5,242,951; 5,116,621 and 5,082,663.

SUMMARY OF THE INVENTION

Methods of producing a terminally sterilized topical patch preparation are provided. In the subject methods, a topical patch preparation is exposed to electron beam radiation, preferably low level electron beam radiation, for a period of time sufficient to terminally sterilize the topical patch preparation. Also provided are the terminally sterilized topical patch preparations produced by the subject methods, as well as methods of using the same.

DESCRIPTION OF THE SPECIFIC EMBODIMENTS

Methods of producing a terminally sterilized topical patch preparation are provided. In the subject methods, a topical patch preparation is exposed to electron beam radiation, preferably low level electron beam radiation, for a period of time sufficient to terminally sterilize the topical patch preparation. Also provided are the terminally sterilized topical patch preparations produced by the subject methods, as well as methods of using the same. In further disclosing the subject invention, methods for producing the subject topical patches and the patches themselves will be described first in greater detail, followed by a review of representative methods of using the topical patches.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Method Of Producing A Terminally Sterilized Topical Patch Preparation

As summarized above, the subject invention provides methods for producing terminally sterilized topical patch preparations. The subject methods are suitable for use in terminally sterilizing a variety of different types of topical patch preparations. By topical patch preparation is meant a composition that includes an active ingredient in a topical delivery vehicle, i.e., a vehicle that is suitable for application to a skin surface (or epidermal surface) of an animal. A variety of different topical patch preparations are known to those of skill in the art. Representative topical patch preparations that may be terminally sterilizable according to the subject methods are provided infra. In many embodiments, the topical patch preparation is present in a sealed packaging means, i.e., it is sealed, as described in greater detail infra.

A feature of the subject methods is that the topical patch preparation, which in many embodiments is sealed in a packaging means, is exposed to electron beam irradiation for a period of time sufficient to terminally sterilize the composition while maintaining the activity of the active agent present therein. The topical patch preparation may be exposed to electron beam irradiation using any convenient protocol and device, where representative protocols and devices for exposing compositions of matter to electron beam irradiation are disclosed in U.S. Pat. Nos. 6,030,554; 6,028,242; 5,989,498 and 5,807,491; the disclosures of which are herein incorporated by reference. In many embodiments, the topical patch composition is exposed to low level electron beam irradiation. By low level electron beam irradiation is meant electron beam irradiation ranging in strength from about 5 to 19 kGy, and in many embodiments from about 8 to 15 kGy.

In practicing the subject methods, the topical patch preparation is exposed to electron beam irradiation for a period of time sufficient to terminally sterilize the topical patch preparation without adversely affecting the properties of the preparation to an unacceptable degree. Generally, the period of time during which the topical patch preparation is exposed to the electron beam irradiation is at least about 1 min., usually at least about 1–2 min. and more usually at least about 2 min., where the period of time may be as long as 3 min. or longer, but usually does not exceed about 5 min. and more usually does not exceed about 3 min. In many embodiments, the period of time ranges from about 1 to 3 and usually from about 1 to 2 min.

The above described process produces a terminally sterilized topical patch preparation. By "terminally sterilized" is meant that the topical patch preparation is substantially, if not completely, free of viable microorganisms, where by "substantially free" is meant that amount of viable microorganisms present in the patch preparation following the above described treatment does not exceed about 100, usually does not exceed about 10 and more usually does not exceed about 5 and by "completely free" is meant that no viable microorganisms are present in the topical patch preparation. As such, the subject patches are substantially, if not completely, free of microorganisms selected from the group consisting of: *Staphylococcus aureus; Psedlomonas aeruginosa; Escherichia coli; Candida albicans; Aspergillus niger*; and the like.

The subject methods are suitable for use in the sterilization of a wide variety of topical patch preparations. Examples of different types of topical patch preparations with which the subject sterilization methods may be employed include those described in U.S. Pat. Nos. 5,827,529; 5,480,646; 5,242,951; 5,116,621; and 5,082,663; the disclosures of which are herein incorporated by reference.

A representative topical patch preparation described in at least some of the above mentioned patents that may be terminally sterilized according to the subject methods is made up of active agent retaining layer present on a support, where the active agent retaining layer is made up of one or more active agents present in, e.g., dissolved in or dispersed in, and adhesive gel base, where the adhesive gel base is made up of a water-soluble high molecular weight substance, water and a water retaining agent.

Water-soluble high molecular weight substances include water-soluble polymers, where polymers of interest include, but are not limited to: gelatin, starch, agar, mannan, alginic acid, polyacrylic acid, polyacrylate, dextrin, methylcellulose, sodium methylcellulose, sodium carboxymethylcellulose, carboxyvinyl polymer, polyvinyl alcohol, polyvinylpyrrolidone, acacia, tragacanth, karaya gum, and starch acrylate copolymer. Metallic salts of these, as well as the products of cross-linking these by means of organic or inorganic cross-linking agents, are also of interest. These water-soluble polymers can be used to bring out the properties and characteristics of the other starting materials used in the adhesive gel composition, and in practice can be used alone or in combinations of 2 or more. The amount of water soluble high molecular weight substance(s) present in the adhesive gel base generally ranges from about 0.5 to 50, usually from a bout 5 to 25% by weight.

The amount of water present in the gel adhesive is sufficient to impart the desired physical properties to the gel adhesive, and generally ranges from about 10 to 70%, usually from about 20 to 50%.

The water-retaining agent or water-holding agent of the subject adhesive gel compositions is any agent that is capable of at least diminishing the volatilization of water contained in the adhesive gel base so that the water content in the adhesive gel base is maintained at least a substantially constant, if not constant, level during storage and use of the preparation. One or more water-retaining agents may be employed in the subject compositions, where the amount of water-retaining agent present in the adhesive gel base generally ranges from about 1 to 70%, more preferably 10 to 60% by weight. Examples of suitable water-retaining or water-holding agents include, but are not limited to: 1 or more types of polyvalent alcohols, such as glycerin, sorbitol, propylene glycol, 1,3-butylene glycol, and ethylene glycol, and the like.

Furthermore, in addition to the aforementioned ingredients, various additives that are used in ordinary topical water-soluble patch preparations may also be suitably compounded as needed, including inorganic substances such as kaolin, bentonite, and titanium dioxide; preservatives such as paraben; anionic, cationic, and nonionic surfactants; metallic aluminum crosslinking agents such as aluminum chloride, dried aluminum hydroxide gel, and dihydroxyaluminum aminoacetate; oils such as jojoba oil and castor oil; solubilizers such as crotamiton; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents.

A diverse array of active agents or ingredients may be present in the adhesive gel base, described supra, in the subject topical patch preparations. Depending on the nature of the agent, the amount of active agent present in the composition generally ranges from about 0.2 to 10%, usually from about 0.2 to 5% and more usually from about 0.5 to 5%. Representative specific active agents of interest include, but are not limited to: dl-camphor, capsaicin, eucalyptus oil, nonivamide, methyl salicylate, glycol salicylate, dipotassium glycyrrhizinate, 1-menthol, and tocopheryl acetate; nonsteroidal antiinflammatories such as salts and derivatives of ketoprofen, flurbiprofen, felbinac, and diclofenac; and local anesthetics such as lidocaine, tetracaine, and xylocaine.

In many embodiments, the active agent present in the composition is a local anesthetic. Although two or more local anesthetic agents may be present in the subject compositions, generally the subject compositions will comprise a single local anesthetic agent. Local anesthetics of interest are those which, when administered in the topical formulations, rapidly penetrate a keratinized skin surface. In many embodiments, local anesthetics of interest have a molecular weight and melting point that is compatible with transport across the keratinized skin surface. Generally, the molecular weight of the local anesthetic will not exceed about 300 dal, and will more usually not exceed about 250 dal. The melting point of the local anesthetic will be less than about 100° C. In many embodiments, the local anesthetic will be a compound comprised of a secondary or tertiary amine linked by a bond or through a connecting group to an aromatic group. The local anesthetic will generally be an alkanyl compound of from about 9 to 20 carbon atoms. Because the composition is applied topically, the local anesthetic will generally be present in the composition as a free base to promote penetration of the agent through the skin surface. A large number of local anesthetics are known in the art, many of which are suitable for topical application. Suitable local anesthetics include lidocaine, butamben, butanilicaine, ethyl aminobenzoate, fomocaine, hydroxyprocaine, isobutyl p-aminobenzoate, naepaine, octacaine, parethoxycaine, piridocaine, prilocaine, procaine, risocaine, tolycaine, trimecaine, tetracaine, xylocaine, ethylaminobenzoate (benzocaine); etc.

As mentioned above, the adhesive gel composition containing the one or more active ingredients is typically present on a support. The support is generally made of a flexible material which is capable of fitting in the movement of human body and includes, for example, various nonwoven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like.

In many embodiments, the to be sterilized topical preparation or patch is present in a sealed package prior to exposure to electron beam irradiation, as described above. Generally, the sealed package is fabricated from a packaging material that includes a layer made out of a material capable of preventing passage of moisture, oxygen and other agents, i.e., the package includes in a moisture/oxygen barrier material. Any suitable barrier material may be employed, where barrier materials of interest include metalic layers, e.g., aluminum, where in many embodiments, the barrier layer is an aluminum layer. This barrier layer has a thickness sufficient to provide for the barrier function, where the thickness typically ranges from about 5 to 15, usually from about 6 to 10 μm. In many embodiments, the package is a laminate of the barrier layer in combination with one or more additional layers, e.g., polymeric layers, paper layers, etc. A representative aluminum containing package that may be used with the subject patch preparations is sold by Dainippon Printing Co., Ltd. (Kyoto, Japan).

The topical patch preparations that may be terminally sterilized according to the subject methods may be fabricated using any convenient protocol. One convenient protocol for fabrication of such patches includes preparing a gel adhesive paste through the uniform mixing of the aforementioned ingredients and then coating the paste onto support, followed by cutting of the resultant product to the specified size to obtain the desired topical patch preparation. The resultant topical patch preparation is then heat-sealed, typically several sheets to a package, using a packaging material containing an aluminum layer, as described supra, to obtain the sealed topical patch. For a more detailed description of the fabrication protocol, see U.S. Pat. No. 5,827,529; the disclosure of which is herein incorporated by reference.

Terminally Sterilized Topical Patch Preparation

Also provided by the subject invention are terminally sterilized patch preparations, where in many embodiments the patch preparations are terminally sterilized packaged patch preparations, i.e., patch preparations sealed in a package, such as an aluminum foil containing package or envelope, as described supra. Because of the process employed in the subject methods, the subject topical preparations are characterized by the presence of non-viable microorganisms and substantially no viable microorganisms, where in certain embodiments the subject terminally sterilized topical patch preparations include no viable microorganisms. Where the subject terminally sterilized topical patch preparations contain some viable microorganisms, they will not contain so many organisms that they cannot be called terminally sterilized. As such, in these embodiments, the number of microorganisms will not exceed about 100, usually will not exceed about 10 and more usually will not exceed about 1 to 10. Because the subject compositions are prepared from non-sterile components and then terminally sterilized, as opposed to preparations prepared under clean room conditions and protocols, the number of non-viable or irradiation killed microorganisms present in the subject compositions is substantial, and may range from about 1 to 100, usually from about 1 to 50 and more usually from about 1 to 10.

Methods Of Using Patch Preparations

The subject terminally sterilized patch preparations find use in the topical delivery of active agents to a host, where by topical delivery is meant delivery via absorption through the skin. In using the subject terminally sterilized topical patch preparations to topically administer an active agent to the skin, the topical preparation is applied to a skin surface and maintained at the site of application for a period of time sufficient for the desired amount of active agent to be delivered to the host, where the period of time typically ranges from about 1 hr to 24 hr, usually from about 1 hr to 12 hr.

Kits

Also provided are kits, where the subject kits at least include one or more terminally sterilized topical patch preparations, as described above. The subject topical patch preparations in the kits may be present in a package, as described supra. The subject kits also generally include instructions for how to use the patches in active agent delivery to a host. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

The following practical and comparative examples are offered by way of illustration and not by way of limitation.

EXPERIMENTAL

I. COMPOSITIONS FOR PRACTICAL EXAMPLES

TABLE 1

Compositions of Practical Examples 1–6.

| Ingredient | Practical Example 1 | Practical Example 2 | Practical Example 3 | Practical Example 4 | Practical Example 5 | Practical Example 6 |
| --- | --- | --- | --- | --- | --- | --- |
| indomethacin | 0.5 | | | | | |
| felbinac | | 0.5 | | | | |
| lidocaine | | | 5.0 | | | |
| glycol salicylate | | | | 1.0 | | |
| l-menthol | 0.5 | | | 0.5 | 0.02 | |
| dl-camphor | | | | 0.5 | | |
| tocopheryl acetate | | | | 0.2 | 0.2 | |
| hyaluronic acid | | | | | 2.0 | |
| crotamiton | 2.0 | 0.5 | | | | |

TABLE 1-continued

Compositions of Practical Examples 1–6.

| Ingredient | Practical Example 1 | Practical Example 2 | Practical Example 3 | Practical Example 4 | Practical Example 5 | Practical Example 6 |
|---|---|---|---|---|---|---|
| sorbitol | 30.0 | 25.0 | 20.0 | 10.0 | | 20.0 |
| kaolin | 5.0 | | 1.5 | 2.0 | | 1.0 |
| urea | | | | 3.0 | | |
| gelatin | | | 2.0 | 1.0 | | 0.5 |
| disodium EDTA | 0.2 | 0.1 | 0.1 | 0.07 | 0.05 | 0.08 |
| diisopropanolamine | | 3.0 | | | | |
| tartaric acid | 2.3 | 0.2 | 1.5 | 1.0 | 1.4 | 1.5 |
| castor oil | 1.0 | 0.2 | | 2.0 | 2.0 | 1.0 |
| Tween-80 | 0.2 | | | 0.2 | | 0.1 |
| methyl paraoxybenzoate | 0.2 | 0.2 | 0.2 | 0.2 | 0.15 | 0.2 |
| dihydroxyaluminum aminoacetate | 0.2 | 0.5 | 0.25 | 0.08 | 0.05 | 0.07 |
| carboxycarbonyl polymer | | 1.6 | | | 0.8 | 0.5 |
| polyacrylic acid | | | 10.0 | 10.0 | | 5.0 |
| sodium polyacrylate | 5.0 | 3.0 | 5.0 | 7.0 | 7.0 | 5.0 |
| sodium carboxymethylcellulose | 4.0 | | 5.0 | 4.0 | 3.0 | 5.0 |
| PVA | 2.0 | 1.0 | 2.0 | | | 1.0 |
| glycerin | 15.0 | 17.0 | 23.0 | 20.0 | 30.0 | 20.0 |
| distilled water | 31.9 | 47.2 | 21.45 | 40.25 | 53.33 | 39.05 |
| Total | 100.00 | 100.00 | 100.00 | 100.00 | 100.00 | 100.00 |

Units are all % w/w.

II. PRACTICAL EXAMPLES

Practical Example 1

A water-soluble polymer gel topical patch preparation is prepared wherein the non-steroidal anti-inflammatory indomethacin is compounded as the active ingredient. All the ingredients are blended together to produce a uniform paste. The paste is spread onto a PET non-woven cloth in an amount of 1200 kg/m$^2$, and the resultant product is then covered with a PP film and cut to a size of 10 cm by 14 cm. These sheets are then packaged, 2 sheets per package, by means of heat sealing in a packaging material containing an aluminum layer. The resulting sealed package product is then irradiated for 2 minutes with a 12 kGy electron beam and thereby sterilized.

Practical Example 2

A water-soluble polymer gel topical patch preparation is prepared wherein the non-steroidal anti-inflammatory felbinac is compounded as the active ingredient. All the ingredients are blended together to produce a uniform paste. The paste is spread onto a PET non-woven cloth in an amount of 1200 kg/m$^2$, and the resulting product is then covered with a PP film and cut to a size of 10 cm by 14 cm. These sheets are then packaged, 2 sheets per package, by means of heat sealing in a packaging material containing an aluminum layer. The resulting packaged product is then irradiated for 2 minutes with a 12 kGy electron beam and thereby sterilized.

Practical Example 3

A water-soluble polymer gel topical patch preparation is prepared wherein the local anesthetic lidocaine is compounded as the active ingredient. All the ingredients are blended together to produce a uniform paste. The paste is spread onto a PET non-woven cloth in an amount of 1200 kg/m$^2$, and the resulting product is then covered with a PP film and cut to a size of 10 cm by 14 cm. These sheets are then packaged, 2 sheets per package, by means of heat sealing in a packaging material containing an aluminum layer. The resultant packaged product is then irradiated for 2 minutes with a 12 kGy electron beam and thereby sterilized.

Practical Example 4

An anti-inflammatory analgesic water-soluble polymer gel topical patch preparation is prepared wherein glycol salicylate, 1-menthol, dl-camphor, and tocopheryl acetate are compounded as the active ingredients. All the ingredients are blended together to produce a uniform paste. The paste is spread onto a PET nonwoven cloth in an amount of 1200 kg/m$^2$, and the resulting product is then covered with a PP film and cut to a size of 10 cm by 14 cm. These sheets are then packaged, 2 sheets per package, by means of heat sealing in a packaging material containing an aluminum layer. The resultant packaged product is then irradiated for 2 minutes with a 12 kGy electron beam and thereby sterilized.

Practical Example 5

A water-soluble, moisture-retaining topical patch preparation is prepared wherein hyaluronic acid and tocopheryl acetate are compounded as the active ingredients. All the ingredients are blended together to produce a uniform paste. The paste is spread onto a PET non-woven cloth in an amount of 1200 kg/m$^2$, and the resulting product is then covered with a PP film and cut to a size of 10 cm by 14 cm. These sheets are then packaged, 2 sheets per package, by means of heat sealing in a packaging material containing an aluminum layer. The resultant packaged product is then irradiated for 2 minutes with a 12 kGy electron beam and thereby sterilized.

Practical Example 6

A placebo. All the ingredients are blended together to produce a uniform paste. The paste is spread onto a PET non-woven cloth in an amount of 1200 kg/m$^2$, and the resulting product is then covered with a PP film and cut to a size of 10 cm by 14 cm. These sheets are then packaged, 2 sheets per package, by means of heat sealing in a packaging material containing an aluminum layer. The resultant packaged product is then irradiated for 2 minutes with a 12 kGy electron beam and thereby sterilized.

III. COMPARATIVE EXAMPLES

Comparative Example 1

A water-soluble polymer gel topical patch preparation according to Practical Example 1 that has not been subjected to sterilization by means of electron beam irradiation.

Comparative Example 2

A water-soluble polymer gel topical patch preparation according to Practical Example 2 that has not been subjected to sterilization by means of electron beam irradiation.

Comparative Example 3

A water-soluble polymer gel topical patch preparation according to Practical Example 3 that has not been subjected to sterilization by means of electron beam irradiation.

Comparative Example 4

A water-soluble polymer gel topical patch preparation according to Practical Example 4 that has not been subjected to sterilization by means of electron beam irradiation.

Comparative Example 5

A water-soluble water-retaining topical patch preparation according to Practical Example 5 that has not been subjected to sterilization by means of electron beam irradiation.

Comparative Example 6

A placebo according to Practical Example 6 that has not been subjected to sterilization by means of electron beam irradiation.

Comparative Example 7

Methyl paraoxybenzoate is added as a preservative in an amount of 0.2% to a water-soluble polymer gel topical patch preparation according to Practical Example 1, and the resulting product is packaged, 2 sheets per package, by means of heat sealing in a packaging material containing an aluminum layer. The resulting product is not subjected to sterilization by means of electron beam irradiation.

Comparative Example 8

Methyl paraoxybenzoate is added as a preservative in an amount of 0.2% to a water-soluble polymer gel topical patch preparation according to Practical Example 2, and the resulting product is packaged, 2 sheets per package, by means of heat sealing in a packaging material containing an aluminum layer. The resulting product is not subjected to sterilization by means of electron beam irradiation.

Comparative Example 9

Methyl paraoxybenzoate is added as a preservative in an amount of 0.2% to a water-soluble polymer gel topical patch preparation according to Practical Example 3, and the resulting product is packaged, 2 sheets per package, by means of heat sealing in a packaging material containing an aluminum layer. The resulting product is not subjected to sterilization by means of electron beam irradiation.

Comparative Example 10

Methyl paraoxybenzoate is added as a preservative in an amount of 0.2% to a water-soluble polymer gel topical patch preparation according to Practical Example 4, and the resulting product is packaged, 2 sheets per package, by means of heat sealing in a packaging material containing an aluminum layer. The resulting product is not subjected to sterilization by means of electron beam irradiation.

Comparative Example 11

Methyl paraoxybenzoate is added as a preservative in an amount of 0.2% to a water-soluble water-retaining topical patch preparation according to Practical Example 5, and the resulting product is packaged, 2 sheets per package, by means of heat sealing in a packaging material containing an aluminum layer. The resulting product is not subjected to sterilization by means of electron beam irradiation.

Comparative Example 12

Methyl paraoxybenzoate is added as a preservative in an amount of 0.2% to a placebo according to Practical Example 6, and the resulting product is packaged, 2 sheets per package, by means of heat sealing in a packaging material containing an aluminum layer. The resulting product is not subjected to sterilization by means of electron beam irradiation.

IV. RESULTS

TABLE 2

Comparative Results of the Levels of Microorganisms in the Compositions of Practical Examples 1–6 and Comparative Examples 1–6.

|  | First comparison | Second comparison | Third comparison |
| --- | --- | --- | --- |
| Practical Example 1 | − | − | − |
| Comparative Example 1 | + | + | + |
| Practical Example 2 | − | − | − |
| Comparative Example 2 | + | + | + |
| Practical Example 3 | − | − | − |
| Comparative Example 3 | + | + | + |
| Practical Example 4 | − | − | − |
| Comparative Example 4 | + | + | + |
| Practical Example 5 | − | − | − |
| Comparative Example 5 | + | + | + |
| Practical Example 6 | − | − | − |
| Comparative Example 6 | + | + | + |

+ presence of microorganisms at low levels
− complete sterilization

As shown in Table 2, sterilization by electron beam irradiation is complete, demonstrating that an adequate sterilization effect may be obtained even with irradiation for 2 minutes at 12 kGy.

The aforementioned Practical Examples 1 through 6 and Comparative Examples 7 through 12, are prepared and stored each in a room kept at 40° C. The Practical and Comparative Examples are compared after 1 week, 1 month, 3 months, and 6 months for preparation discoloration and abnormal odors (Table 3). For Practical Example 1 and Comparative Example 7, and for Practical Example 3 and Comparative Example 9, the contents of the active ingredients are also measured and compared (Table 4).

The values shown represent the differences between the Practical Examples and the Comparative Examples, and represent the sensory differences felt by 10 healthy individuals comparing the respective examples.

TABLE 3

Comparative Results for Discoloration and Abnormal Odor.

|  | After 1 week | | After 1 month | | After 3 months | | After 6 months | |
|---|---|---|---|---|---|---|---|---|
|  | Discoloration | Abnormal odor | Discoloration | Abnormal odor | Discoloration | Abnormal odor | Discoloration | Abnormal odor |
| Practical Example 1 | − | − | − | − | + | + | + | + |
| Practical Example 2 | − | − | − | − | + | − | + | − |
| Practical Example 3 | − | − | − | − | − | + | + | + |
| Practical Example 4 | − | − | − | − | − | − | − | + |
| Practical Example 5 | − | − | − | − | − | − | + | + |
| Practical Example 6 | − | − | − | − | − | − | − | − |

3+ a considerable difference
2+ a difference
+ a slight difference
− no difference As shown in Table 3, the topical patch preparations subjected to electron beam irradiation sterilization exhibit virtually the same external characteristics as the topical patch preparations that are not subjected to electron beam irradiation sterilization. As such, long-term storage results in, for example, extremely little decomposition of the water-soluble polymer gel due to the electron irradiation.

All of the results shown are obtained by conducting [the comparison] at n=3, and are the means thereof.

TABLE 4

Results of Measurement and Comparison of the Active Ingredients of Practical Example 1 and Comparative Example 7, and of Practical Example 3 and Comparative Example 9.

|  | After 1 week | After 1 month | After 3 months | After 6 months |
|---|---|---|---|---|
| indomethacin |  |  |  |  |
| Practical Example 1 | 4.98 | 4.94 | 4.88 | 4.72 |
| Comparative Example 7 | 4.99 | 4.96 | 4.87 | 4.75 |
| lidocaine |  |  |  |  |
| Practical Example 3 | 48.7 | 48.3 | 47.9 | 47.1 |
| Comparative Example 9 | 49.2 | 48.9 | 48.5 | 47.7 |

Units are mg active ingredient/g composition.

Table 4 shows that, as far as the stability of the active ingredients is concerned, virtually no decomposition is caused by electron beam irradiation, and stability is well within a range of ±10%.

VI. STABILITY

A. Introduction

Three sublots of lidocaine topical patch (5% as described in practical example 3, above) ( lot #2024 ) were subjected respectively to a low E-Beam irradiation dose of 0.5 megarad ( or 5.0 kGy ), 0.9–1.0 megarad ( or 9–10 kGy), and 1.3–1.4 megarad ( 13–14 kGy ).

The three stability lots were recorded as follows:

| Stability No | Irradiation dose |
|---|---|
| 001-9A | 0.5 mrad |
| 001-9b | 0.9–1.0 mrad |
| 001-9C | 1.3–1.4 mrad |

B. Specific Lots

1. STABILITY #001-9A subjected to 5.0 kGy (kilogray) or 0.5 mrad e-beam radiation

| Tests performed | Initial | 3 mo 40° C. | 6 mo 40° C. | Specifications |
|---|---|---|---|---|
| Microbiology |  |  |  |  |
| Sterility tests (USP 24) | Pass | Pass | Pass | Pass |

-continued

| Chemistry | | | | |
|---|---|---|---|---|
| Physical appearances | Pass | Pass | Pass | White to light yellow, faint characteristic odor |
| Lidocaine HCL | 96.4% | 101.3% | 101.4% | 90.0–110.0% of 700 mg per patch |
| Dissolution, lidocaine | 324.2 mg | 321.5 mg | 348.0 mg | NLT 280 mg/patch at 30 minutes |
| Methylparaben | 13.2 mg | 13.6 mg | 13.6 mg | 14.0 +/− 1.4 mg per patch |
| Propylparaben | 6.70 mg | 6.95 mg | 7.12 mg | 7.0 +/− 0.7 mg per patch |
| Related compounds 2,6-xylidine | None detected | None detected | None detected | <700 mcgs/patch |
| pH | 6.80 | 6.95 | 6.82 | 6.0–7.5 |
| Adhesive strength | 38 seconds | 27 seconds | >5 seconds | NLT 5 seconds |
| Weight variation Average (20) RSD | 16.354 g 2.04 g | 16.280 g 1.41 g | 16.390 g 1.62 g | Deviation NMT 10% |

2. STABILITY #001-9B subjected to 9 to 10 kGy (kilogray) or 0.9 to 1.0 mrad (megarad) e-beam radiation.

| Tests performed | Initial | 3 mo 40° C. | 6 mo 40° C. | Specifications |
|---|---|---|---|---|
| Microbiology | | | | |
| Sterility tests (USP 24) | Pass | Pass | Pass | Pass |
| Chemistry | | | | |
| Physical appearances | Pass | Pass | Pass | White to light yellow, faint characteristic odor |
| Lidocaine HCL | 96.7% | 103.2% | 100.8% | 90.0–110.0% of 700 mg per patch |
| Dissolution, lidocaine | 344.6 mg per patch | 328.8 mg per patch | 349.7 mg per patch | NLT 280 mg per patch |
| Methylparaben | 13.5 mg | 13.9 mg | 13.4 mg | 14.0 +/− 1.4 mg per patch |
| Propylparaben | 6.51 mg | 7.09 mg | 7.04 mg | 7.0 +/− 0.7 mg per patch |
| Related compounds 2,6-xylidine | None detected | None detected | None detected | <700 mcg/patch |
| pH | 6.81 | 7.10 | 6.83 | 6.0–7.5 |
| Adhesive strength | 39 seconds | 22 seconds | >5 seconds | NLT 5 seconds |
| Weight variation Average(20) RSD | 16.389 g 1.54 g | 16.470 g 1.71 g | 16.504 g 1.45 g | Deviation NMT 10% |

3. STABILITY #001-9C subjected to 13 to 14 kGy (kilogray) or 1.3 to 1.4 megarad e-beam radiation

| Tests performed | Initial | 3 mo 40° C. | 6 mo 40° C. | Specifications |
|---|---|---|---|---|
| Microbiology | | | | |
| Sterility tests (USP 24) | Pass | Pass | Pass | Pass |
| Chemistry | | | | |
| Physical appearances | Pass | Pass | Pass | White to light yellow, faint characteristic odor |
| Lidocaine HCL | 96.6% | 98.3% | 97.7% | 90.0–110.0% of 700 mg per patch |
| Dissolution, lidocaine | 328.5 mg | 334.5 mg | 332.9 mg | NLT 280 mg per patch |
| Methylparaben | 13.5 mg | 13.5 mg | 13.3 mg | 14 +/− 1.4 mg per patch |

| -continued | | | |
|---|---|---|---|
| Propylparaben | 6.52 mg | 6.85 mg | 6.97 mg | 7 +/− 0.7 mg per patch |
| Related compounds 2,6-xylidine | None detected | None detected | None detected | <700 mcgs per patch |
| pH | 6.79 | 7.00 | 6.81 | 6.0–7.5 |
| Adhesive strength | 60 seconds | 46 seconds | >5 seconds | NLT 5 seconds |
| Weight variation | 16.409 g | 16.290 g | 16.389 mg | Deviation |
| Average (20) RSD | 1.33 g | 1.88 mg | 1.58 mg | NMT 10% |

C. Results

Storage at accelerated conditions (6 months 40° C. 75% RH) of the lidocaine patch 5% subjected to e-beam radiation from a dose of 0.5 to 1.4 megarad shows no effects on the stability and the sterility of the product.

It is evident from the above results and discussion that the subject invention provides for the effective, complete sterilization of a topical patch preparation using electron beam radiation, even at low levels of irradiation, whereby a stable, terminally sterilized topical patch preparation is produced. As such, the subject invention provides a more convenient method for producing terminally sterilized topical patch. Furthermore, the subject terminally sterilized patch preparations have a broad ranges of diverse applications because of their terminal sterility, where such applications include applications to open wounds, etc. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a scaled, terminally sterilized topical patch preparation, said method comprising:

(a) producing a sealed topical patch preparation by the method comprising:
(i) providing a topical patch preparation comprising:
(a) an active agent retaining layer comprising a pharmaceutically active agent; and
(b) a support for said active agent retaining layer;
(ii) packaging said topical patch preparation in packaging material comprising an aluminum layer; and
(iii) sealing said packaged topical patch preparation; and (b) exposing said sealed topical patch preparation to low level electron beam radiation for a period of time sufficient to terminally sterilize said topical patch preparation;

to produce a scaled, terminally sterilized topical patch preparation.

2. The method of claim 1, wherein said low level electron beam radiation ranges from about 5 to 19 kGy.

3. The method of claim 1, wherein said low level electron beam radiation ranges about 8 to 15 kGy.

4. The method of claim 1, wherein said preparation is exposed for a period of time ranging from about 40 to 80 sec.

5. A scaled, terminally sterilized topical patch preparation produced according to the method of claim 1.

* * * * *